(12) United States Patent
Ivanov et al.

(10) Patent No.: US 6,820,400 B2
(45) Date of Patent: Nov. 23, 2004

(54) PACKAGE WINDER INSERTER

(75) Inventors: Konstantin Ivanov, Basking Ridge, NJ (US); John Rega, Milltown, NJ (US); Clifford Dey, Flemington, NJ (US); Albert C. Grosenbeck, Easton, PA (US); Robert J. Cerwin, Pipersville, PA (US); Joseph Stanley Siernos, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/125,029

(22) Filed: Apr. 18, 2002

(65) Prior Publication Data

US 2003/0196416 A1 Oct. 23, 2003

(51) Int. Cl.⁷ .............................. B65B 5/00; B65B 63/04
(52) U.S. Cl. .............................. 53/473; 53/430; 53/250; 53/251
(58) Field of Search ........................... 53/118, 117, 116, 53/430, 250, 251, 473

(56) References Cited

U.S. PATENT DOCUMENTS

| | | | | |
|---|---|---|---|---|
| 5,228,565 A | * | 7/1993 | Sinn | 206/63.3 |
| 5,359,831 A | * | 11/1994 | Brown et al. | 53/430 |
| 5,442,896 A | * | 8/1995 | Sinn | 53/430 |
| 5,461,844 A | * | 10/1995 | Brown | 53/449 |
| 5,473,854 A | * | 12/1995 | Demarest et al. | 53/116 |
| 5,487,212 A | * | 1/1996 | Demarest et al. | 29/407.05 |
| 5,491,954 A | * | 2/1996 | Sobel | 53/116 |
| 5,491,955 A | | 2/1996 | Sobel | |
| 5,675,961 A | * | 10/1997 | Cerwin et al. | 53/430 |
| 5,956,927 A | * | 9/1999 | Daniele et al. | 53/430 |
| 5,987,848 A | | 11/1999 | Branco | |
| 6,014,851 A | | 1/2000 | Branco | |
| 6,029,806 A | * | 2/2000 | Cerwin et al. | 206/63.3 |
| 6,032,343 A | | 3/2000 | Branco | |
| 6,138,440 A | * | 10/2000 | Gemma | 53/430 |
| 6,205,748 B1 | * | 3/2001 | Daniele et al. | 53/430 |
| 6,463,719 B2 | * | 10/2002 | Dey et al. | 53/430 |

FOREIGN PATENT DOCUMENTS

EP    1 214 912 A    6/2002

OTHER PUBLICATIONS

European Search Report EP 03 25 2490 dated Aug. 18, 2003.

* cited by examiner

Primary Examiner—Scott A. Smith
Assistant Examiner—Gloria R Weeks
(74) Attorney, Agent, or Firm—Emil Richard Skula

(57) ABSTRACT

An apparatus for inserting surgical needles in needle parks. The apparatus has a frame, a needle block slidably mounted to the frame, a shuttle member slidably mounted to the frame, and a pick-up head. The needle block has a plurality of guide members spaced apart to receive at least one surgical needle and at least one needle park. The apparatus is used in a method of automatically loading surgical needles into the needle parks of surgical suture packages.

11 Claims, 17 Drawing Sheets

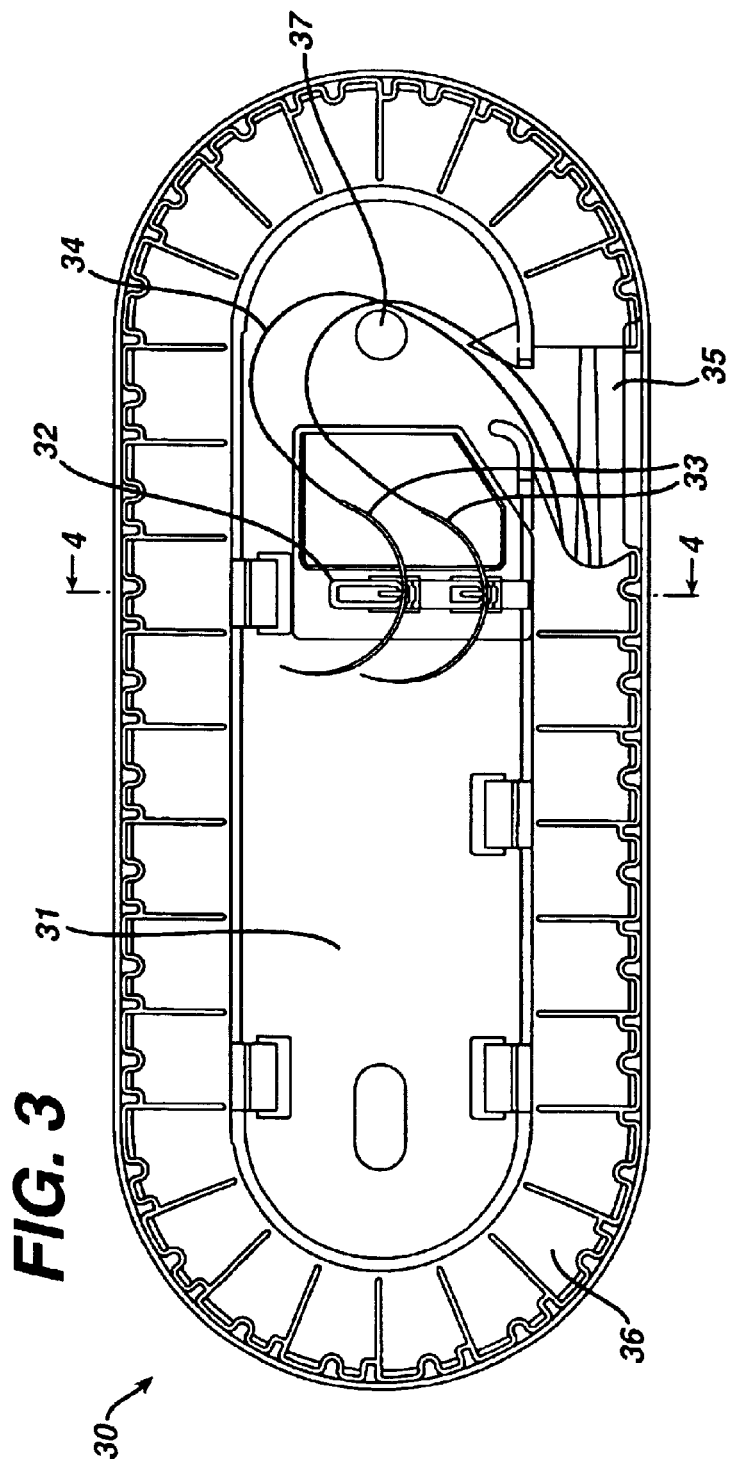
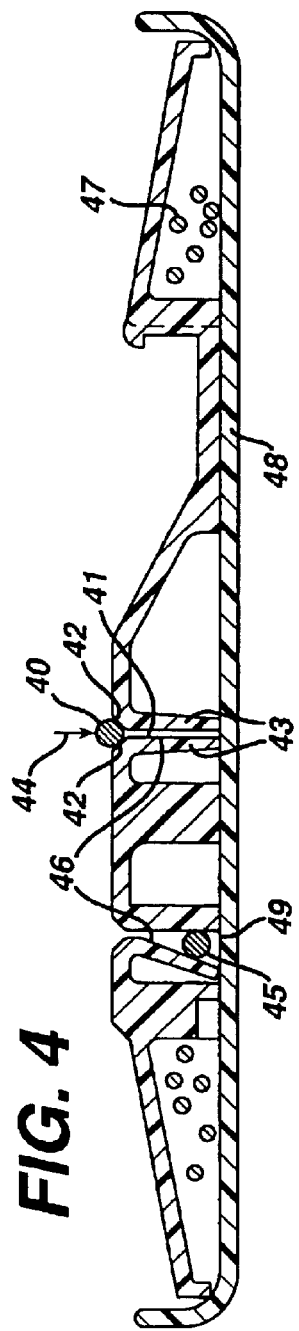
FIG. 3
FIG. 4

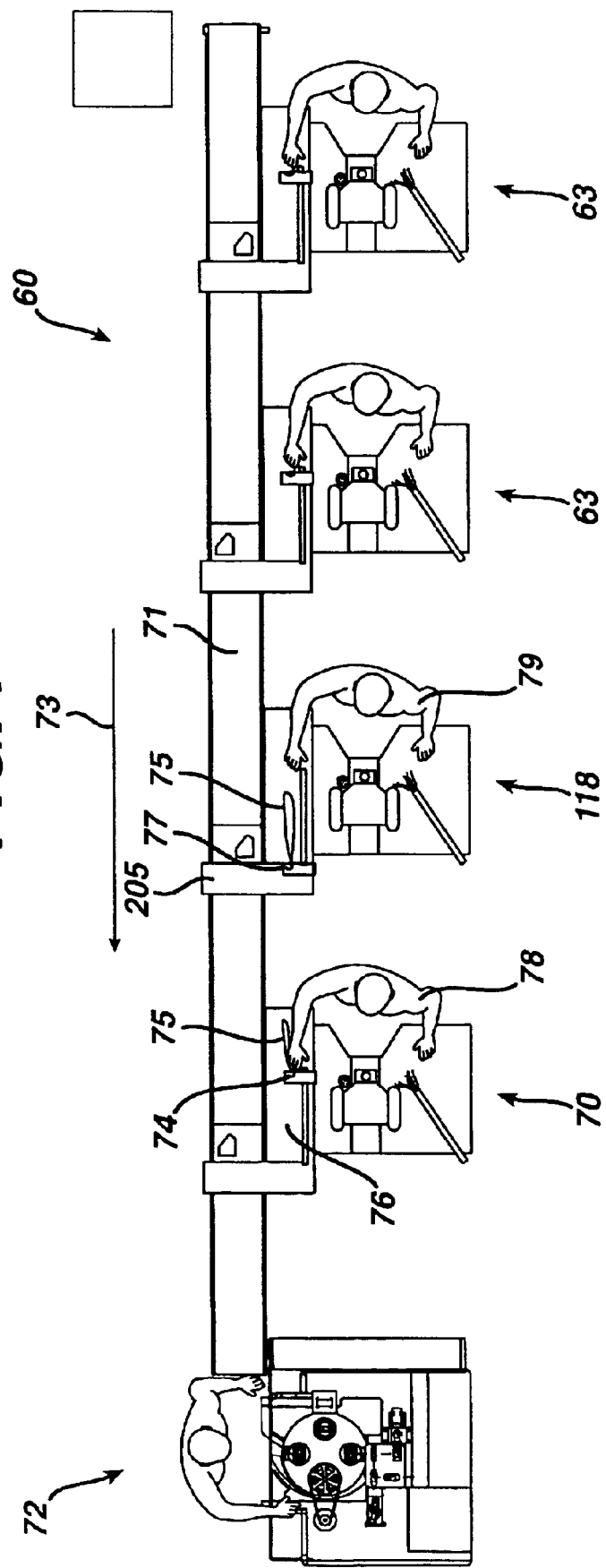

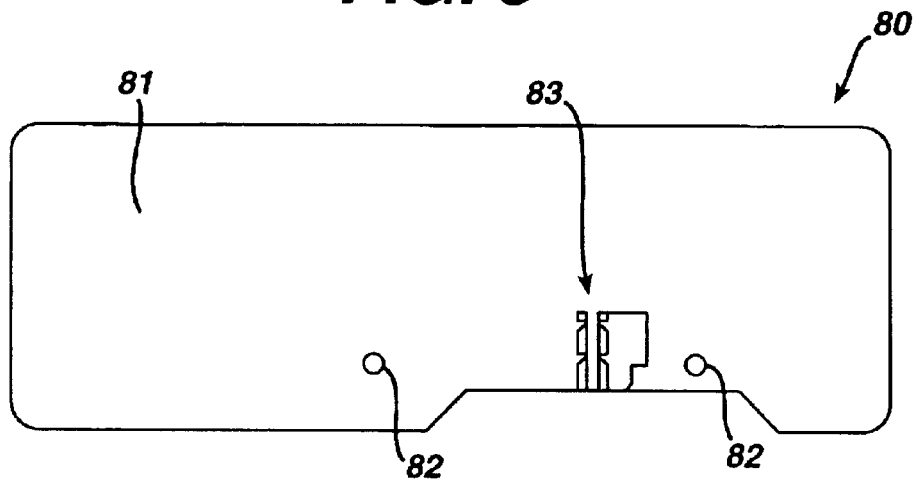
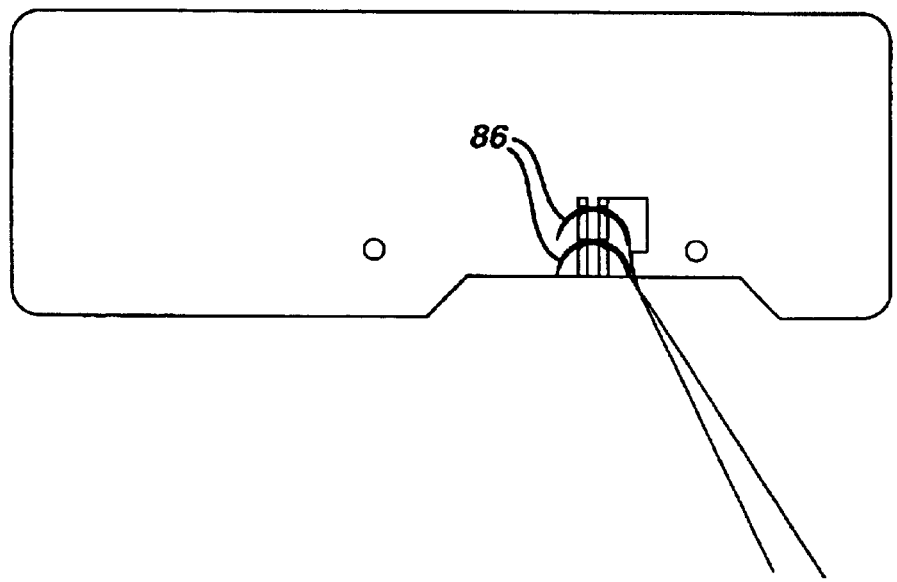

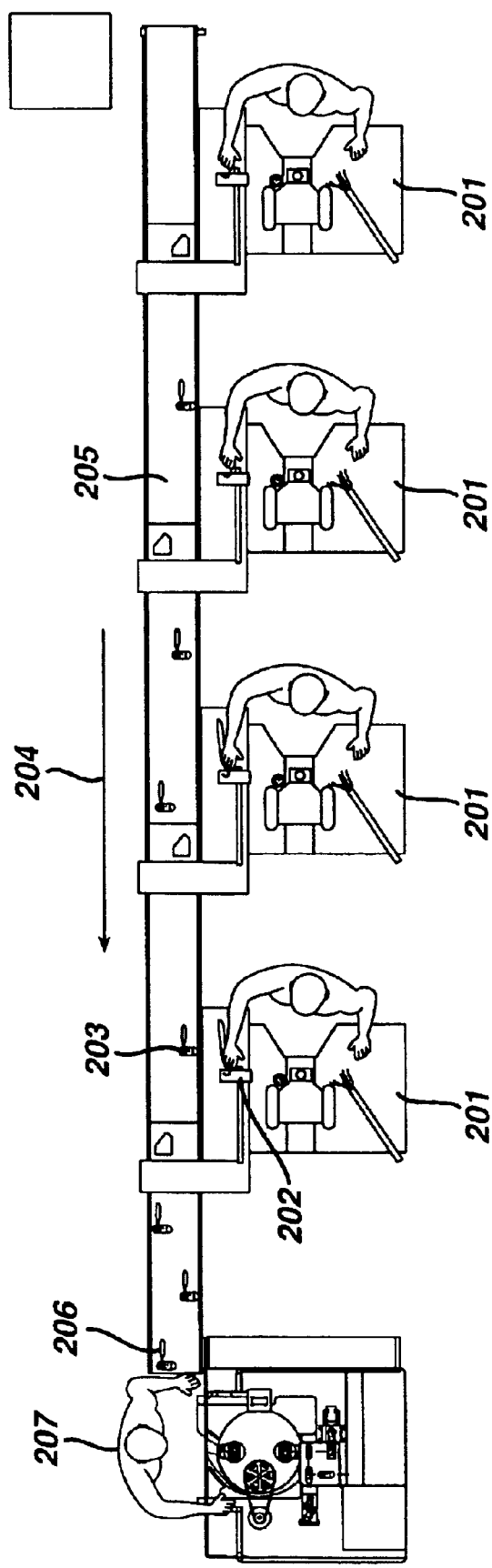

PACKAGE WINDER INSERTER

TECHNICAL FIELD

This invention relates to packaging machinery and processes for assembling and packaging medical devices, in particular, the packaging of surgical sutures.

BACKGROUND OF THE INVENTION

Surgical sutures having needles attached are well known in the medical field. Sutures conventionally used may have one needle attached to the suture strand, or two needles, one on each end. Surgical needles are typically packaged in conventional packages. Such packages typically have sections for receiving the suture and structures conventionally referred to as needle parks for receiving surgical needles.

Most existing packaging processes require that needles be manually placed in needle parks prior to winding or placing sutures in a package. This can result in damage to the needles and sutures, and it is a tedious task that can be fatiguing to the operator. In addition, transportation of needles and attached sutures from a conventional swaging or attachment apparatus to the packaging station results in additional handling and the possibility of in-process damage to needles.

Accordingly, there is a need for novel improved processes and apparatuses for automatically placing needles in needle parks.

SUMMARY OF THE INVENTION

Therefore, it is the object of the present invention to provide a novel apparatus and method to mechanically connect a needle swaging operation with a loading and winding and packaging machine, thereby eliminating the in-process inventory of conventional felt lined trays and carts described hereinbelow, and minimizing the chances for mixing product and subjecting it to contamination and damage from extra handling steps.

It is yet another object of the present invention to reduce the skill and potential for ergonomic stress of an operator by mechanizing the task of needle insertion into the package needle-park.

Still yet another object of the present invention is to improve suture packaging machine efficiency and production output by removing the tedious task of manual needle insertion into a needle-park, and to minimize interruption thereof from mis-loads and operator fatigue.

Accordingly, a machine or apparatus that receives swaged needle suture assemblies from a manual swaging operator, automatically loads needles into surgical suture package needle-parks, and transports these partial assemblies to a packaging machine operator is disclosed. A plurality of the machines may optionally link several swaging stations to one packaging machine in order to balance production rates. An optional mechanical belt conveyor is configured to transport packages with needles pre-loaded from the swaging presses and apparatuses of the present invention to the machine loading station. The conveyor also providing a buffering function to smooth imbalances of the production rate compared to the winding machine. The apparatus of the present invention for loading surgical needles into surgical suture packages has a machine frame. There is a needle block member having a top surface and a bottom surface, the needle block member is slidably mounted to the frame. A plurality of needle guide members extend up from the top surface of the needle block member, the guide members are spaced apart to receive at least one surgical needle. The needle guide members have contact surfaces, and the guide members are additionally spaced apart to receive at least one needle park. A shuttle member is slidably mounted to the frame for engaging and moving a suture package. A pick-up head is slidably mounted to the frame for picking up the package from the shuttle member, and contacting the package with the needle block member such that the needle park of the package is located between the needle guide members. The pick-up head is moveable horizontally as well as vertically. Preferably the pick-up head has a vacuum cavity.

Another aspect of the present invention is a method of loading a surgical needle into a needle park of a surgical suture package using the above-described apparatus.

These and other aspects and advantages of the present invention will become apparent from the following description and accompanying drawings.

BRIEF DESCRIPTION OF THE DRAWINGS

FIG. 3 illustrates a conventional assembled suture package, after processing by a known winding/packaging machine.

FIG. 4 is an enlarged cross section view of the package of FIG. 3 taken at section A—A.

FIG. 7 illustrates the apparatus of present invention in combination with conventional suture swaging and winding operations.

FIG. 8 illustrates a needle block component of the present invention.

FIG. 9 illustrates the needle block with needles and sutures installed therein.

FIG. 23 is a plan view of the present invention applied to suture swaging and winding operations, illustrating assembled product on the conveyor.

DESCRIPTION OF THE PREFERRED EMBODIMENTS

Figure 1A:
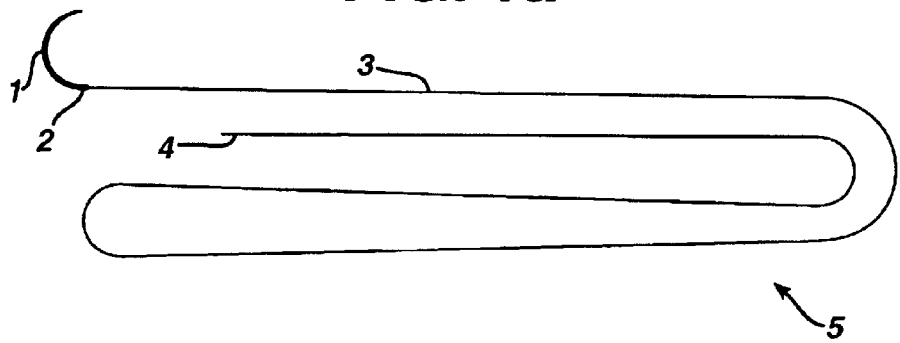
FIGS. 1a and 1b illustrate conventional surgical sutures with needles attached, and features thereof.

FIG. 1a illustrates a conventional surgical suture with an attached needle. The assembly 5 is seen to have a needle 1, butt or barrel end of the needle and the area of suture attachment 2, suture strand 3, and suture trailing end 4. This assembly 5 is conventionally referred to as a "single-armed suture". This name is derived from the characteristic that the assembly 5 has a single needle attached to one end only of the suture.

Figure 1B:
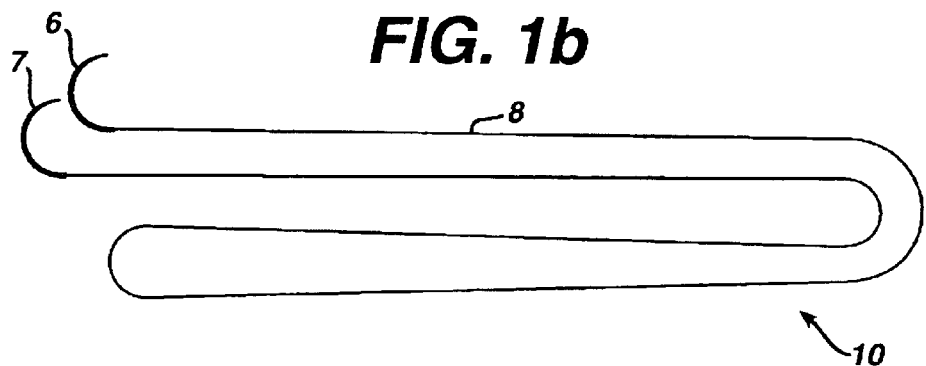

FIG. 1b illustrates a similar surgical suture 8 with two attached needles 6 and 7, one on each end of the suture 8, comprising assembly 10. This assembly is referred to as a "double-armed suture", derived from the characteristic that it has two needles 6 and 7 attached, one to each end of the suture 8.

Figure 2:
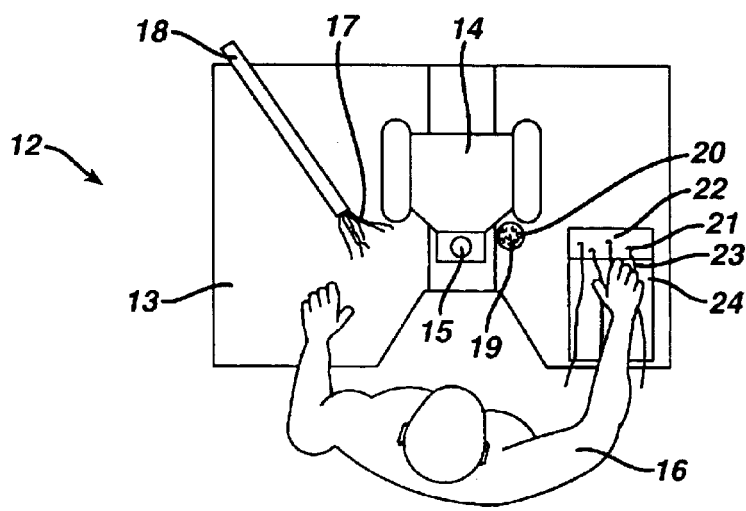
FIG. 2 illustrates a conventional manual needle-swaging machine configured for production utilizing a conventional process.

Sutures are attached to needles by a conventional manufacturing process referred to as "swaging", employing the use of a conventional manual workstation as seen in FIG. 2. Said workstation is seen to have a table 13, mechanical press 14, and tooling 15. In operation, the operator 16 grasps a suture strand 17 from the holding tube 18, while simultaneously picking a needle 19 from the tray 20. The operator 16 manually positions a suture end into the needle attachment feature, typically an axially drilled hole or formed side channel (not shown), places this combination into the press tooling 15, and activates the press for one or more strokes, thereby crimping the metallic needle swage area 2 (FIG. 1a) and fixing said needle to said suture strand, forming the needle suture assembly 5. Double-armed sutures are assembled by performing the needle swaging procedure hereinabove on each end of the suture, forming needle/suture assembly 10.

As seen in FIG. 2, completed needle suture assemblies 21 are delivered in a conventional manner to the next manufacturing operation, typically suture winding, described hereinbelow. The storing and holding method for this delivery must protect fragile needle points and suture strands, avoid exposure to foreign material, provide a means of maintaining production batch identity, and provide accessibility for efficient handling.

One such conventional method used for delivering swaged needle/suture assemblies to a package winding operation employs the use of a foam pad 22 into which swaged needle assemblies 21 are placed, the points of the needle axially thrust by hand until penetration is adequate to secure the needle suture assembly to withstand handling movements, the position of said pad 22 arranged so as to allow the suture strands 23 attached thereto to lay into a flat tray 24 lined with felt or other soft material. Said trays 24 may be stacked on carts or other transportation means and delivered to the package winding operation.

A conventional suture package 30 having a winding track is illustrated in FIGS. 3 and 4. The suture package 30 is seen to have a double-armed suture assembled therein. The package has a plastic molded body 31 having winding pin opening 37, into which is molded a double needle-park 32, and an oval suture track 35, covered by a plurality of hinged door flaps 36.

The assembly sequence of packaging surgical needles and sutures into package 30 begins by inserting the needle or needles 33 into the needle-park 32. The sutures attached thereto are then wound into the suture track 35 utilizing conventional rotatingly mounted mechanisms (not shown) in a conventional winding machine.

The insertion of needles into the needle park is illustrated in the enlarged section A—A elevation view of FIG. 4, showing the dual needle-parks 46, sectioned plastic molded package 48, and end sectioned views of the suture strands 47 wound therein. A first needle, shown by the circular cross section of the needle wire 40, is manually positioned above the needle park slot 41 resting on two chamfers 42 that provide lead-in to spread the plastic needle-park legs 43. Downward finger pressure by the winding machine operator in the location and direction of the arrow 44 forces the needle 40 onto the needle-park, until it contacts the floor 49 of the package 30, reaching a position as illustrated for the second needle 45. The second needle 45 is illustrated in the completely installed position, having the needle-park legs 46 fully deformed and springingly applying clamping pressure which retains the needle firmly in the package.

Typical manufacturing packaging procedures include inserting needles into needle parks at the packaging machine loading operation, requiring high finger pressure to deform the needle-park elements and completely seat the needles in place.

Figure 5:
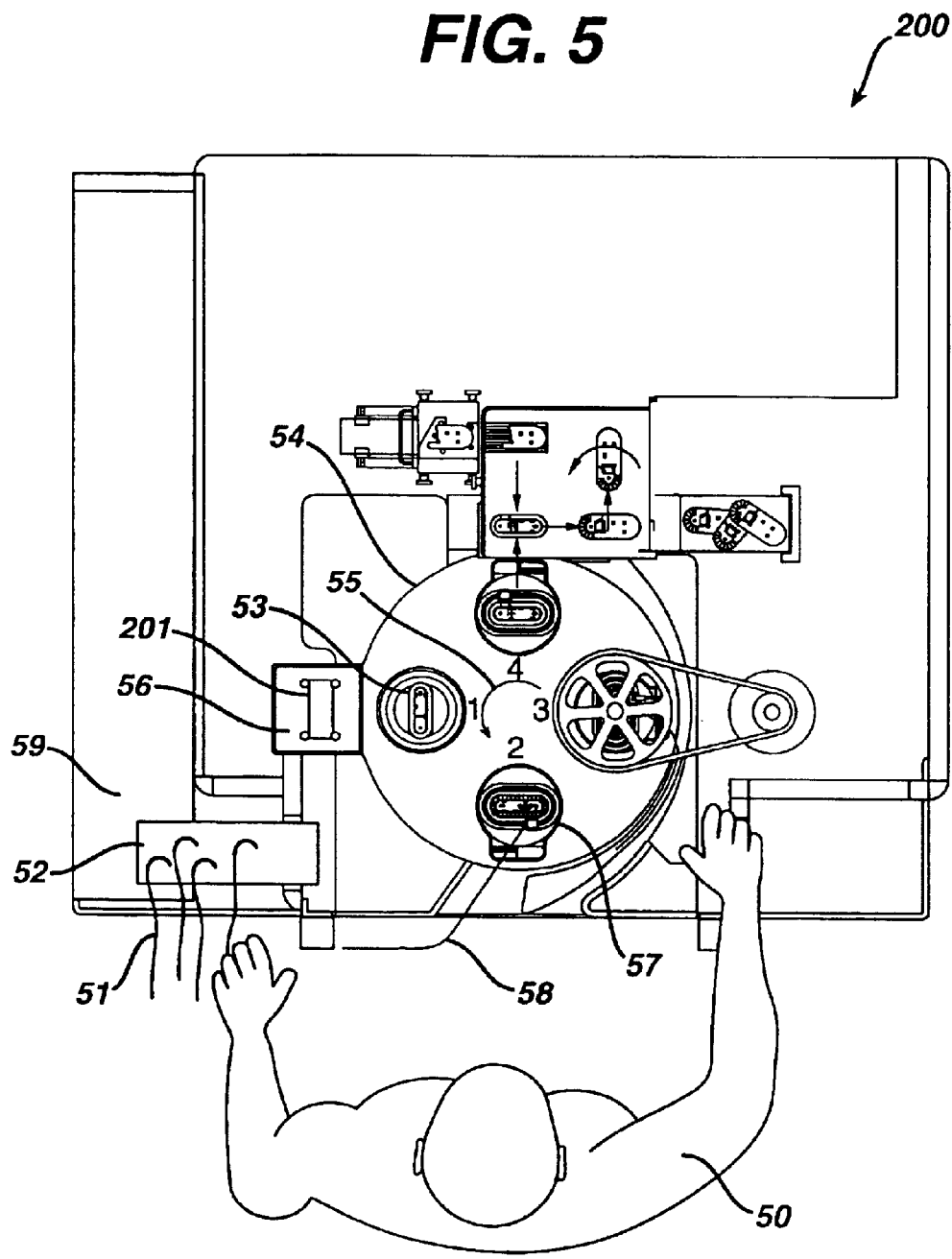
FIG. 5 illustrates a conventional suture winding/packaging machine.

Referring now to FIG. 5, a plan view of a conventional suture winding and packaging machine 200 is illustrated. The machine 200 illustrated in FIG. 5 has a four station indexing turret 54, a vertical hopper 56 containing empty package moldings 201, and a load station 57 in which the operator 50 loads one or two needles into needle parks of packages 201, with the attached suture 58 trailing loosely therebehind. Those skilled in the art will appreciate that other hand loaded machine configurations exist and may be used.

The foam pad with needle/suture assemblies affixed thereto 22 (FIG. 2) as a means of handling are transported to the winding and packaging machine FIG. 56 by various conventional trays and cart methods (not shown). At the winding machine 200, the foam pad 52 (FIG. 5) is placed in a convenient position for handling on the machine top plate 59 as illustrated. The machine operator 50 removes a needle/suture assembly 51 and manually places the needle or needles of assembly 51 with the operator's fingers into the molded package needle park 57 (described in detail in FIG. 4 and text related thereto). The operator cycles the machine 200, causing the turret 55 to index 90°, as indicated by arrow 55, and conventional peripheral machine mechanisms to wind and complete the package (not described in detail), and the machine thereby is prepared for the next cycle.

Manually placing the needles by hand into the package manually at the package machine load station 57 requires a high degree of special finger dexterity and keen eyesight, and exposes the needles to handling damage as they are pressed into the needle-park 57 of the package. Although this relatively labor intensive manual operation can be managed with proper controls and operator skill, it typically slows the packaging machine production rate, thereby reducing process efficiency, and offers potential for damage to the needles and ergonomic stress to the fingers and hands of the human operators.

Figure 6A:
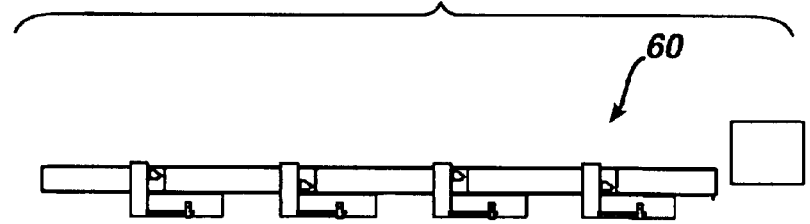
FIGS. 6a and 6b are plan views of an apparatus of present invention.

Referring now to FIG. 6a, a preferred embodiment of an apparatus 60 of the present invention is illustrated. The zipper winder inserter 60 is a manufacturing apparatus that connects multiple production operations into one, thereby achieving a mechanically connected flow of product through a sequence of individual operations, and which eliminates manual loading of needle parks.

Figure 6B:
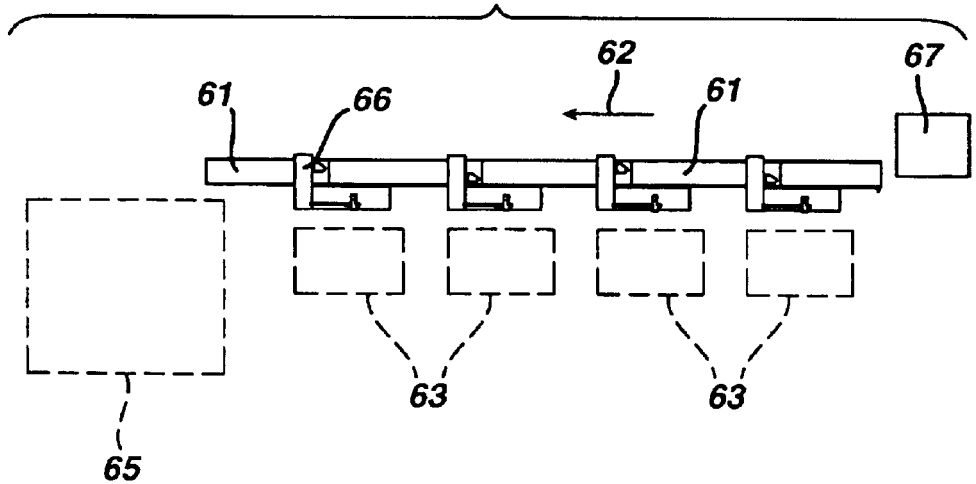

Please refer next to FIG. 6b, which illustrates the zipper winder inserter 60 with peripheral operations related thereto. The zipper winder inserter 60 is seen to have a conveyor 61 (in the preferred embodiment a linear conveyor), moving in the direction of arrow 62. Adjacent to said conveyor 61 is provision for a plurality of workstations 63, illustrated in dashed line. Adjacent to each workstation 63, affixed to said conveyor 61, are manufacturing assembly modules 66, each configured to receive partially assembled product from the adjacent workstation 63, automatically perform additional manufacturing operations on said product, and load the product on the conveyor 61. At the discharge end of the conveyor 61 is provision to affix an assembly, packaging, or other processing machine 65, illustrated also by a dashed line rectangle. The quantity of workstations 63 arrayed along the conveyor 61 is determined by their relative output rate compared to and balanced with the final machine 65. As can be seen in FIG. 6, the length of the conveyor 61, illustrating four workstations 63 for this example, can be extended or shortened to accommodate more or less workstations 63, using this flexibility to achieve the output balance between workstations 63 and a higher output machine 65. Four workstations are illustrated in FIG. 6, as would be, for example, if this particular application produced approximately one fourth the output of one winding machine 65.

Conventional electronic controls 67 perform switching, timing, detection, and cycling functions as needed to operate the various mechanisms for the zipper winder inserter 60, using currently available technology.

The preferred embodiment, described hereinbelow, is the application of the zipper winder inserter machine 60 to the packaging of surgical sutures.

FIG. 7 illustrates the zipper winder inserter machine 60 of FIG. 6 applied to the suture production operations described above. Four manual swaging workstations 63 are positioned along the length of the conveyor 71, and one winding/packaging machine 72 at the discharge end of the conveyor 71 continuously moving in the direction of arrow 73.

FIG. 5 and the text related thereto described a prior art winding machine operation requiring the operator 50 to perform a labor intensive needle loading task as part of each machine cycle. The zipper winder inserter 60 illustrated in FIG. 7 performs this task automatically, thereby allowing a substantial production rate increase of the winding/packaging machine 72 and reduction in operator ergonomic fatigue.

The manual suture swaging workstation 70 illustrated in FIG. 7 operates as described for FIG. 2, with the exception of operator handling of the completed needle/suture assembly after swaging. The swaging workstation operator 78, as seen in FIG. 7, places the needles of the needle/suture assembly into a needle block 74, allowing the suture strands 75 to trail behind on a smooth surface 76.

Illustrations included herein may show one or two needles for clarity in the description. One needle represents operation of the invention when manufacturing a single armed suture, two needles a double-armed suture.

FIG. 8, illustrates an enlarged plan view of the needle block 74 of FIG. 7. The objectives of the needle block 80 are to provide a receptacle for the needles, after swaging, that is easy and fast to load manually by the operator, allows the needles to be transported away from the working area of the operator, protects the needle points from damage, and includes design features that allow the needles to be transferred to the package molded needle-park automatically, as described hereinbelow.

The needle block 80 is seen to be a member made from a non-magnetic rigid material such as, but not limited to, a hard structural plastic, finished with a flat surface 81. The surface 81 of needle-block 80 embodies pilot pins 82 pressed into and rising above the surface 81, sized and positioned to engage and mate with pilot holes in the molded package (illustrated hereinbelow). Extending from surface 81 is pins 82.

Figure 10:
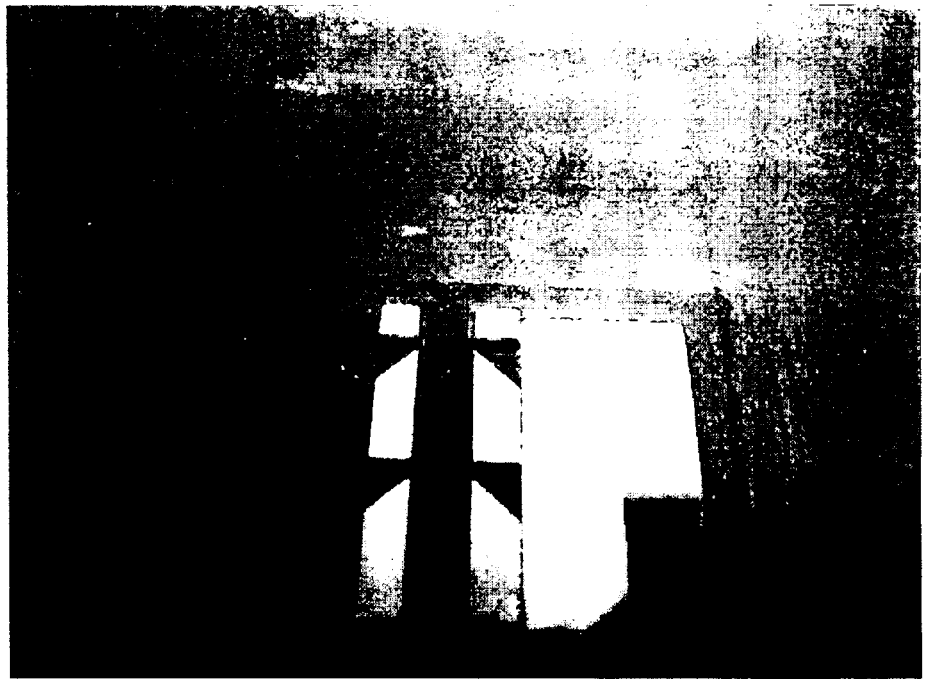
FIG. 10 is a scanned image showing a perspective view of the needle block.
Figure 11:
FIG. 11 is a scanned image showing a perspective view of the needle block with needles and sutures installed therein.

FIG. 9 illustrates the needle block of FIG. 8 with two needles 86 inserted in nest 83. FIGS. 10 and 11 are digital photos (scanned images) of the needle nest 83 section of block 80 illustrated in FIGS. 8 and 9, for visual clarification.

Figure 12:
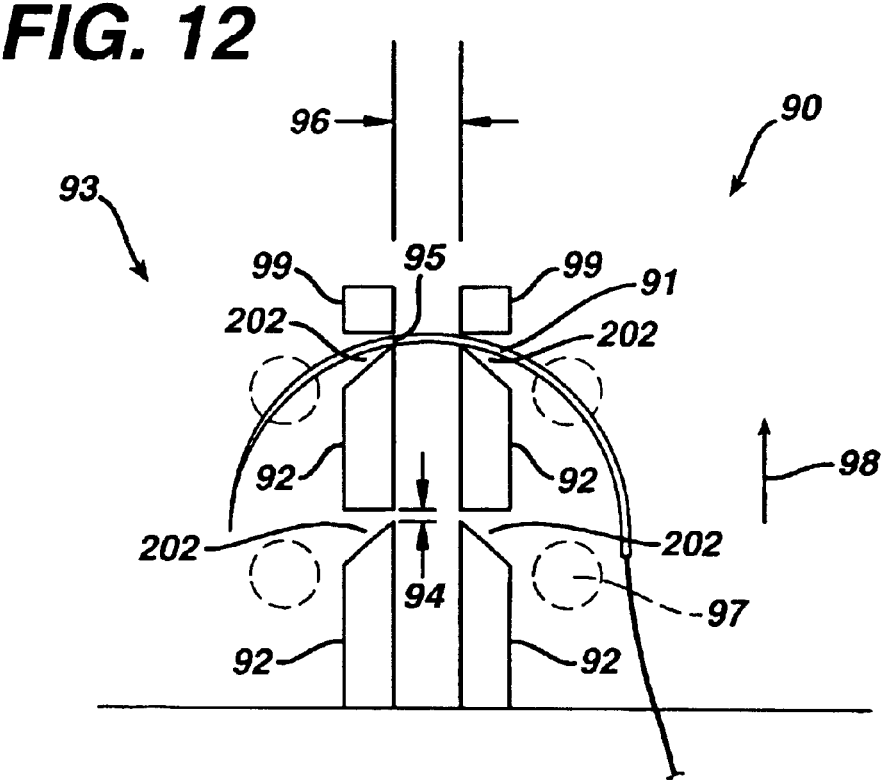
FIG. 12 is an enlarged view of the needle block nest.

FIG. 12 is a further enlarged view of the needle nest 90, illustrating one needle 91 positioned manually therein by the swaging operator. A double-armed suture would have two needles 91 positioned therein. The needle nest 90 is comprised of coplanar, flat topped needle guides 92 and 99 shaped as illustrated and extending to an elevation above the block surface 93. Preferably said elevation is more than one half the largest wire diameter of the needles intended for this process. Identical gaps 94 and 95 are dimensioned to accept the largest needle wire diameter, with additional clearance sufficient to achieve a loose, non-binding fit. The needle guides 92 are shaped to provide angular material clearance 202 on the needle curvature side of gaps 94 and 95, and therefore not interfere with the curvature of the needles 91 positioned in the needle guides 92 and 99. The raised needle guides 92 and 99 have a third gap 96 therebetween, dimensioned to fit outside and thereby straddle the package needle-park, described and illustrated hereinbelow. The front sides of needle guides 92 and 99 are seen to have a flat surface.

The needle guides 92 and 99 of needle block 90 are configured to accept a range of needle sizes, thereby reducing the need for changing the said needle block when different size needles are manufactured.

Figure 12A:
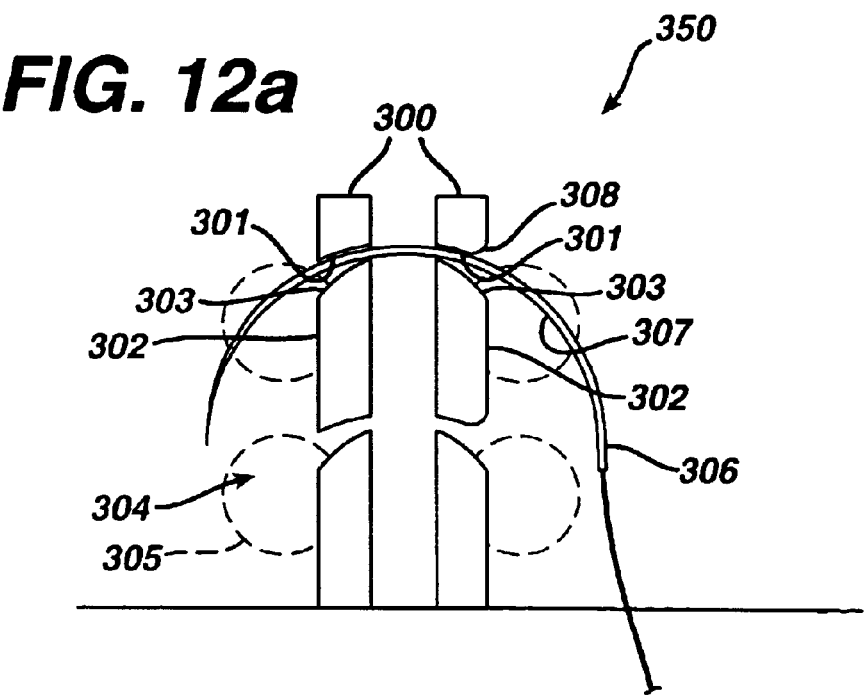
FIG. 12a is an enlarged view of an optional alternate embodiment of the needle block nest of FIG. 12.

FIG. 12a illustrates an optional alternative embodiment of a needle nest 350, having a preferred embodiment for certain needle sizes. Needle guides 300 embody curved surfaces 301, which correspond to the outer curvature diameter 306 of certain larger needles (illustrated), and also embody a lead-in radius 308. Needle guides 302 embody curved surfaces 303, which correspond to the inner curvature diameter 307 of certain smaller needles (not shown). Identical corresponding shapes are embodied in the second needle guides 304 therebelow.

Preferably, in order to enhance engagement of a needle in the needle nest, four cylindrical magnets 97, positioned as shown by the four dashed circles, are pressed into blind vertical holes from the underside of the needle block, said holes drilled close to the surface 93 but not breaking through said surface, and not therefore visible from the top plan view. The design of FIG. 12a embodies four cylindrical magnets 305 as illustrated and described for the needle block of FIG. 12.

To load needles into the nest 90, the manual swaging operator positions a needle or needles 91, individually or together, roughly oriented with points facing as shown, against the top surface of needle guides 92, and proceeds to slide said needles in the direction of arrow 98. When a needle passes the gap 94 or 95 in the guide 92, it will drop into said gap, remaining located as illustrated. The needle 91 are secured in place by the walls of needle guides 92 and 99 surrounding gaps 94 and 95, and by the attracting field of the cylindrical magnets 97 exerting a downward force of the needle wire against the nest surface 93.

It can be seen that the above needle block and loading procedure is relatively fast, simple, not damaging to the needles, and requires no ergonomically stressful downward force compared to the insertion by operator fingers illustrated in FIG. 4 and described in text related thereto.

Please refer to FIG. 7. After inserting the needles as described hereinabove, the manual swaging operator 79 activates a switch (not shown) that initiates one cycle of the individual inserter assembly device 205 for that workstation 118. Said activation commands the machine controller to cause movement of the needle block 74, illustrated at the workstation 70 of the first swaging operator 78, to a position 77, shown for illustration purpose at the workstation of the second swaging operator 79 at the second workstation 118. Movement is driven by an air cylinder or similar conventional actuating device, said movement guided by appropriate rails and slides therebelow.

FIGS. 13 through 16 illustrate the automatic transfer of needles from the needle block to the package.

Figure 13:
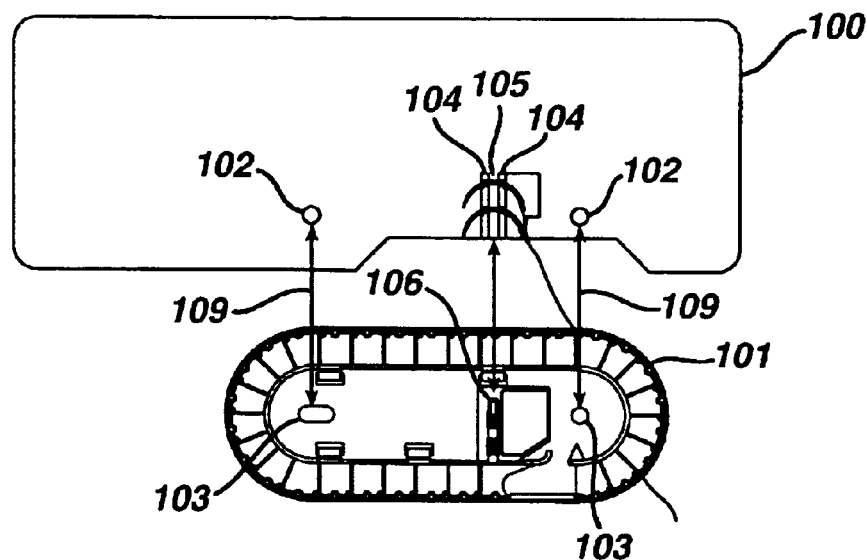
FIGS. 13 through 16 illustrate the automatic transfer of needles from the needle block to a package needle-park.

FIG. 13 illustrates a needle block 100 and a molded suture package 101 placed therebeside. Placement is such that pilot pins 102 in the needle block 100 can be seen congruently aligned with pilot holes 103 in the package molding 101, evident from arrows 109 constructed to illustrate this alignment. Likewise, the needle guides 104, and the gap 105, are aligned and located to straddle the needle-park 106 in the package molding 101 to be inserted therebetween.

Figure 14:
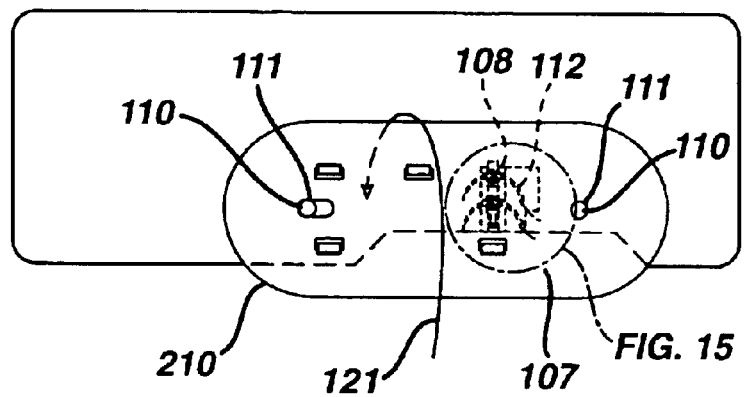
Figure 15:
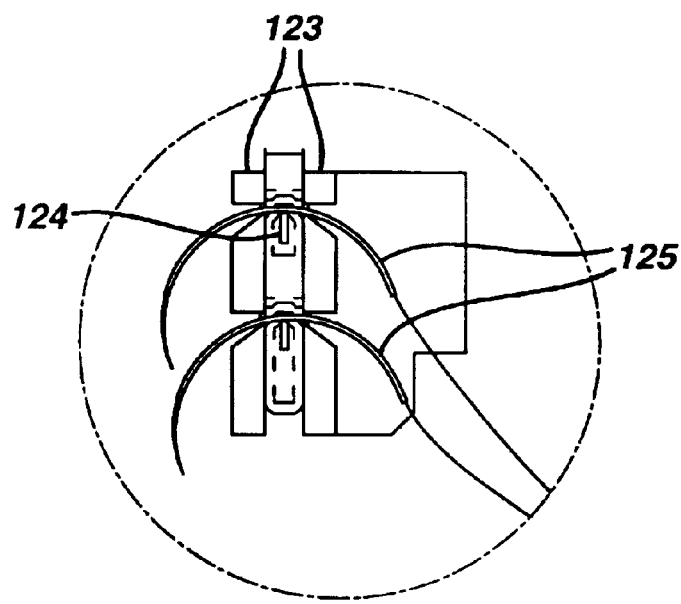
Figure 16:
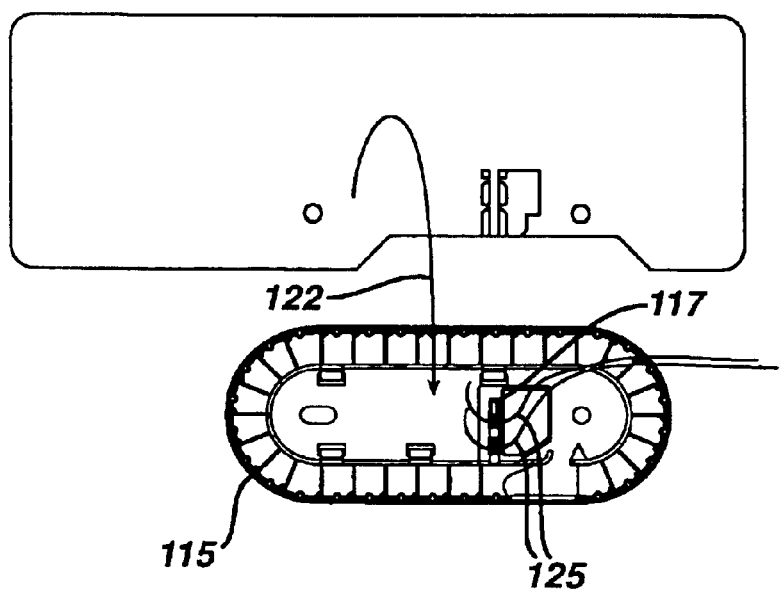

FIG. 14, looking through the plastic package molding, illustrates the package molding 101 of FIG. 13 flipped-over, inverted, as indicated by arrow 121, now oriented with the needle-park side down, and pilot holes 111 placed over tapered pilot pins 110. The needle-park 108 is aligned and fits between needle guides 104. Downward mechanical pressure on the area above the needle-park, illustrated in FIG. 14 with a dashed line 107, will force the needles 112 to be inserted and transferred into the needle-park 108 of the package molding 210. FIG. 15 is an enlarged view of the needle guides 123 and needle-park 124 of FIG. 14, illustrating the needle-park 124 surrounding and engaging the needles 125. Removal and inverting the package molding 115, as indicated by arrow 122 (FIG. 16), illustrates the transfer of needles 116 to the needle-park 117 and insertion therein.

Figure 17:
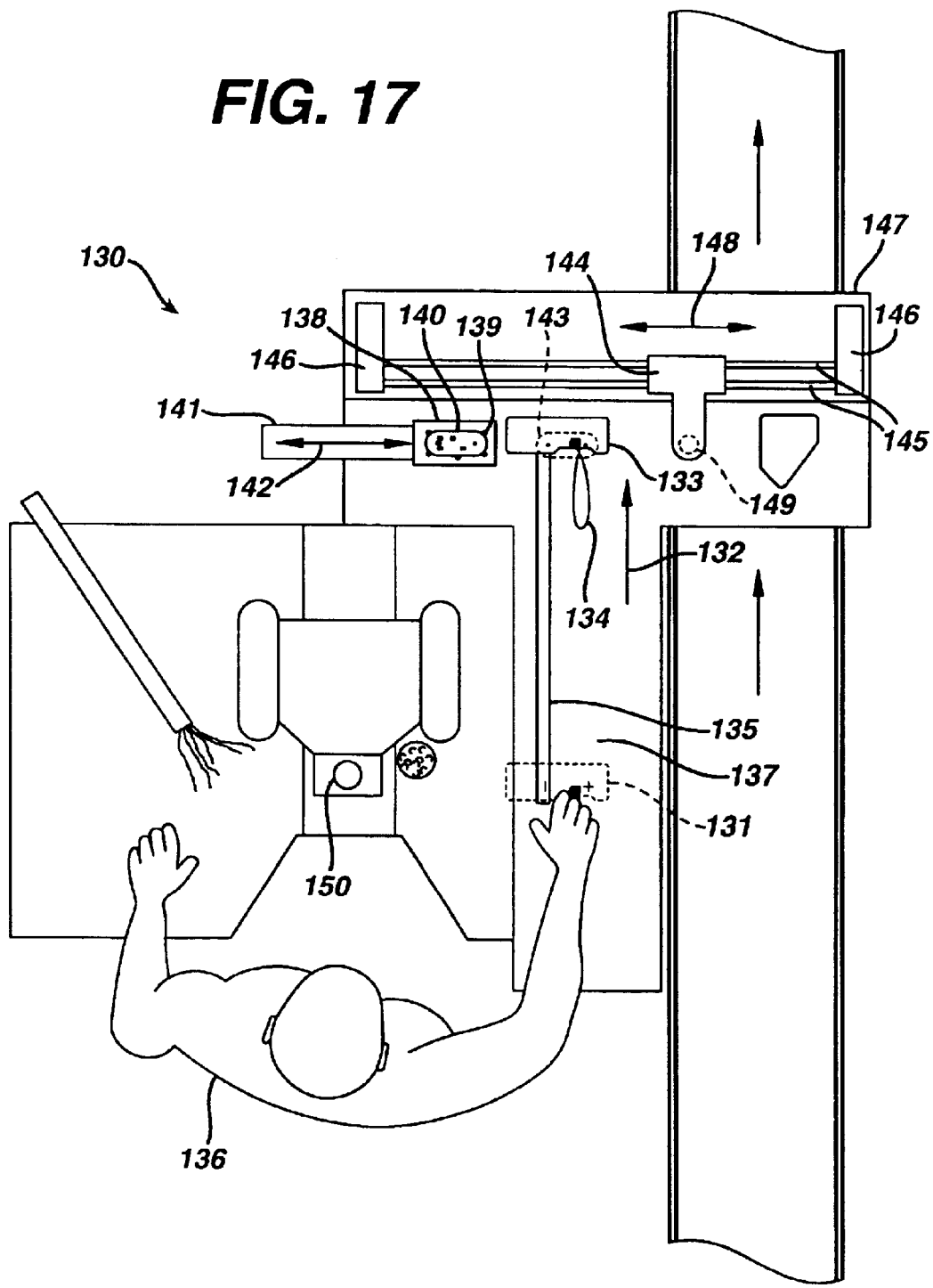
FIG. 17 illustrates a conventional manual needle-swaging machine configured for production utilizing the apparatus of the present invention, prior to machine cycle start.

FIG. 17, illustrates an enlarged view of workstation 118 of FIG. 7. FIG. 17 illustrates detailed mechanisms that perform the needle transfer of FIGS. 13 through 16 to the molded suture package 115 (FIG. 16), and transport said package, with needles inserted and suture attached thereto, to the conveyor and ultimately the winding/packaging machine 72 of FIG. 7.

Conventional motion generating devices and mechanical guidance thereof, including linear slides actuated by air cylinders, electric motors, hydraulics, and other motion devices known in the machine design art, are omitted from detailed description.

The functional sequence consists of the operator 136 completing the needle swaging in the press tooling 150, and placement of needles, with sutures loosely trailing therebehind, into the needle block 131, shown in dashed lines, and activating a switch (not shown) to start the cycle for the assembly mechanisms of workstation 130.

The needle block 131 is driven in the direction of arrow 132, by a linear slide 135, ceasing motion at a stop position 133. The trailing suture loop 134 slides on a soft, clean, surface 137, said surface made of polished steel or a lower-friction plastic surface.

A hopper 138 is filled with a stack of empty molded suture packages 140, confined by a plurality of vertical rods 139, or other suitable structure, configured to render said stack vertically slideable but horizontally fixed. Said packages in said stack are oriented with the needle parks facing down and toward the needle-block 133. Affixed to the base of said hopper is an escapement shuttle 141, slideable, linearly guided, and driven by a motion device (not shown), to the right or left as indicated by arrow 142. Said shuttle embodies a recessed, package sized pocket (not shown) beneath the package stack 140.

Reciprocating motion of the shuttle slide 141, right and left as illustrated by arrow 142, causes a singulating and dispensing function, typical in the machine design industry, of feeders referred to as coin-changer or slice-type. With each cycle one molded package from the stack 140 will be stripped therefrom and fed to the dashed line receiving position 143.

A pickup head 144, slideable in the direction of arrow 148 on rods 145 which are fixedly mounted in support blocks 146 and thereby the machine frame 147, embodies a vacuum cup pickup 149. Said vacuum cup pickup 149 has a powered vertical motion capability incorporated therein (not illustrated).

Refer to FIGS. 18 to 21 for a description of the machine sequence.

Figure 18:
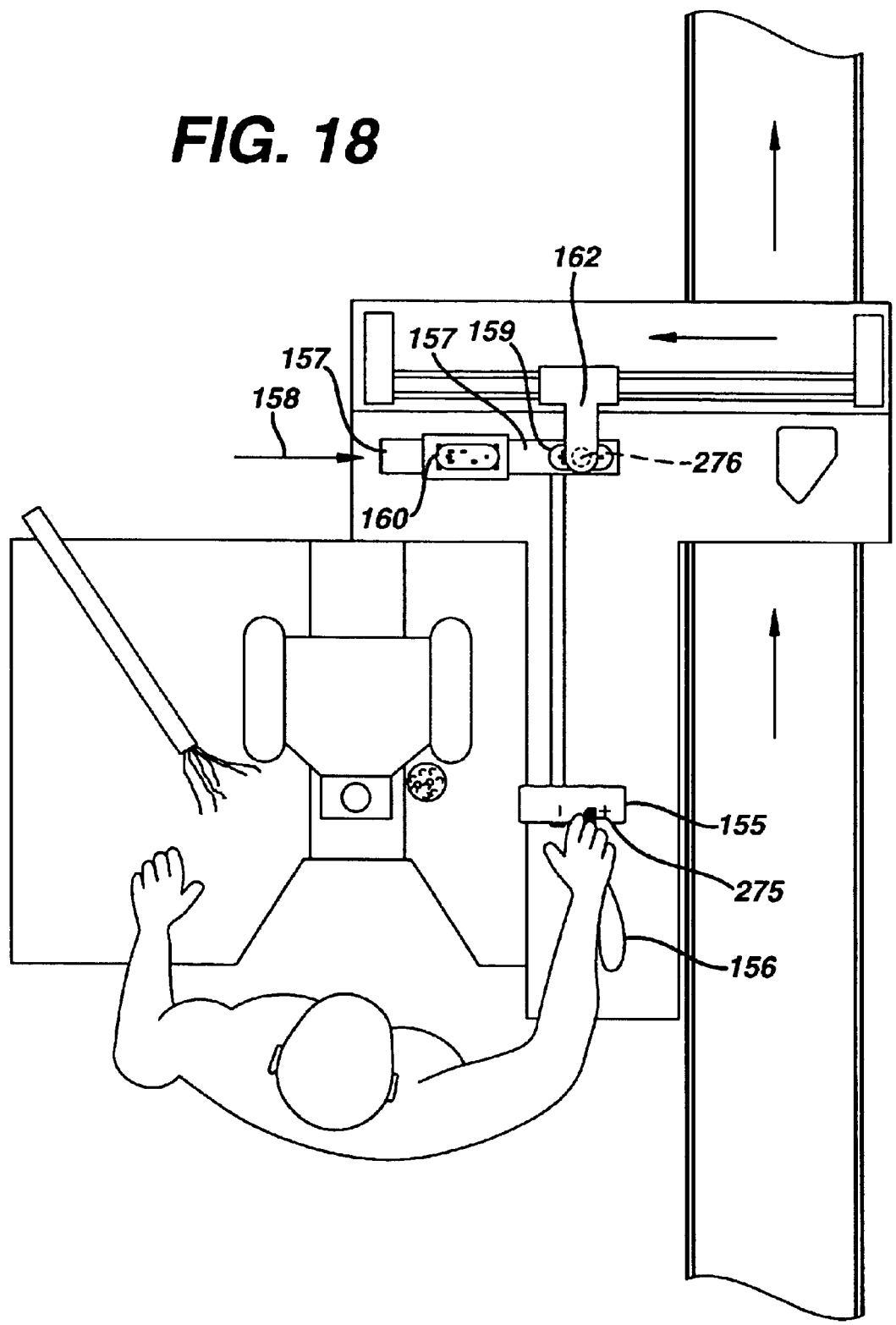
FIGS. 18 through 21 illustrate a manual needle-swaging machine configured for production utilizing the present invention, with the machine cycle underway.

As seen in FIG. 18, the machine is shown in the home or start position with the needle block 155, hand loaded with needles 275, and trailing the suture 156.

Figure 19:
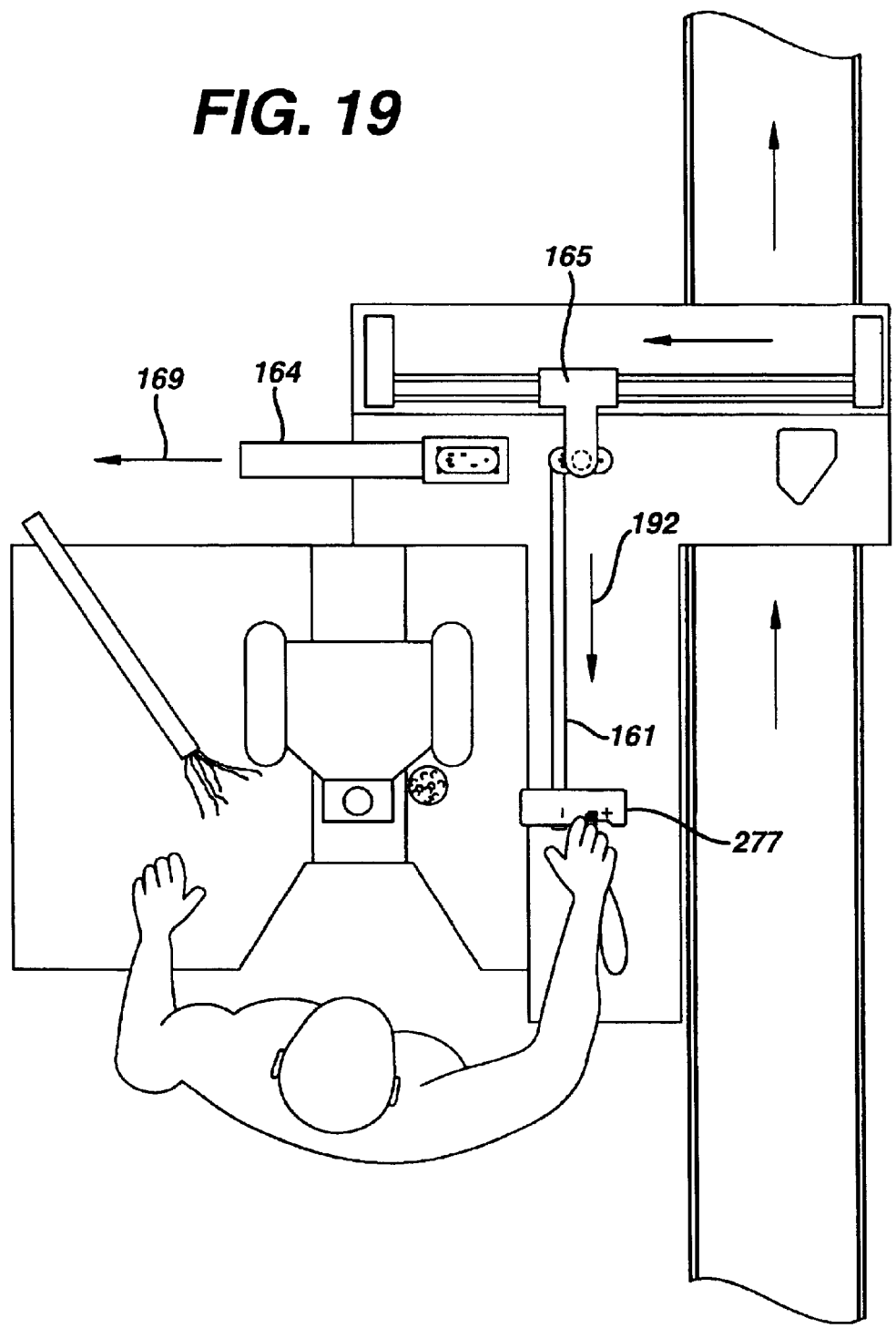

The hopper shuttle 157 has been driven in the direction of arrow 158 and has delivered one package molding 159 from the hopper stack 160. The pick-up head 162 is positioned over the hopper shuttle 157. The operator initiates the cycle, causing the vacuum cup pick-up 276 to lift the package molding 159 from the hopper shuttle 157. Referring now to FIG. 19, the electronic controller moves the hopper shuttle in the direction of arrow 169 to the retract position 164.

Figure 20:
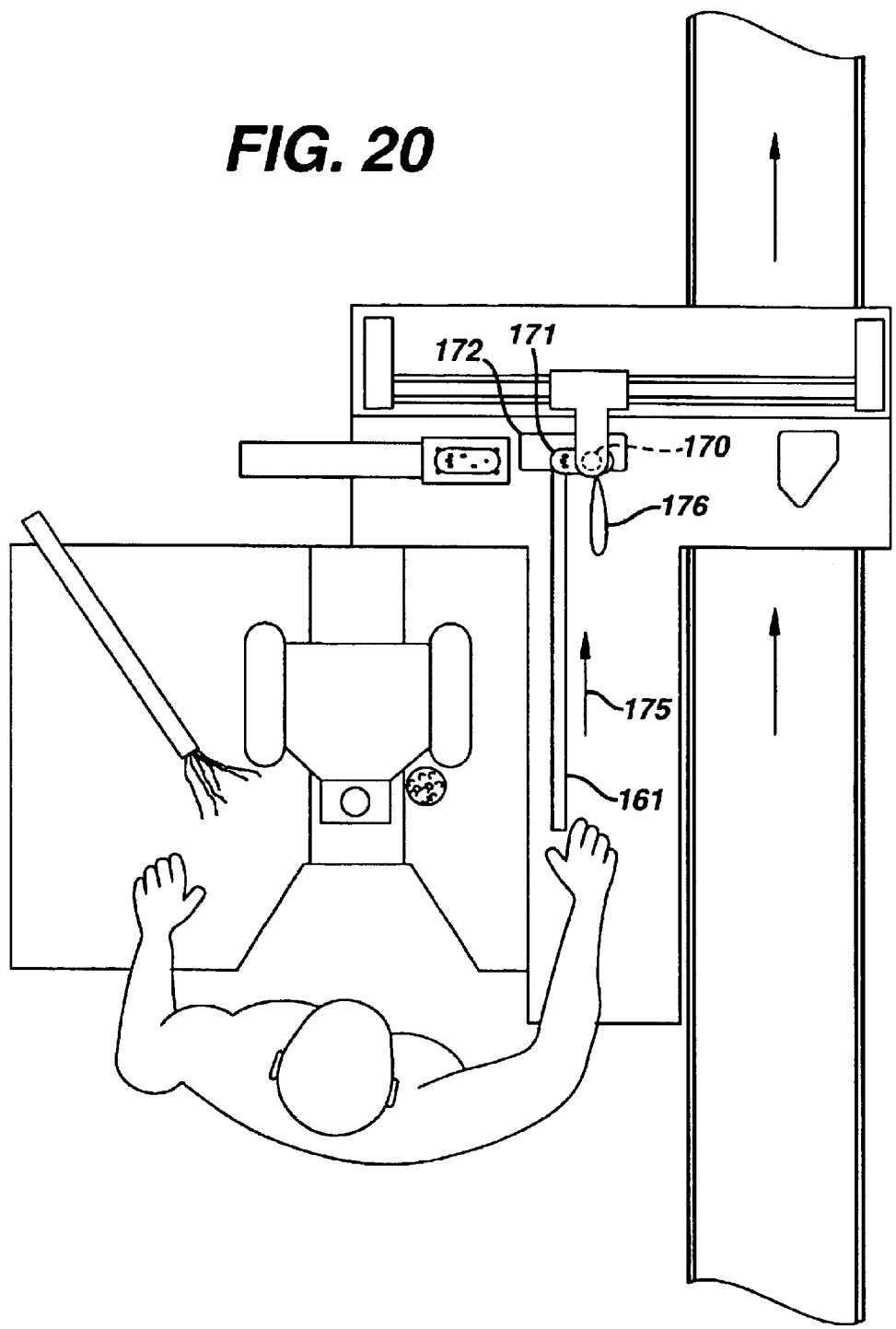

Referring to FIG. 20, continuing the automatic sequence, the needle block 172 moves in the direction of arrow 175, guided by a slide 161, thereby transporting the needles and suture 176 to a position under the molded package 171, gripped by vacuum cup pick-up 170. The vacuum cup pick-up 170 is driven forcibly downward, thereby pressing the molded package needle parks against the needles in the needle block 172, and causing said needles to be inserted in said needle parks as illustrated in FIGS. 13 to 16.

Figure 21:
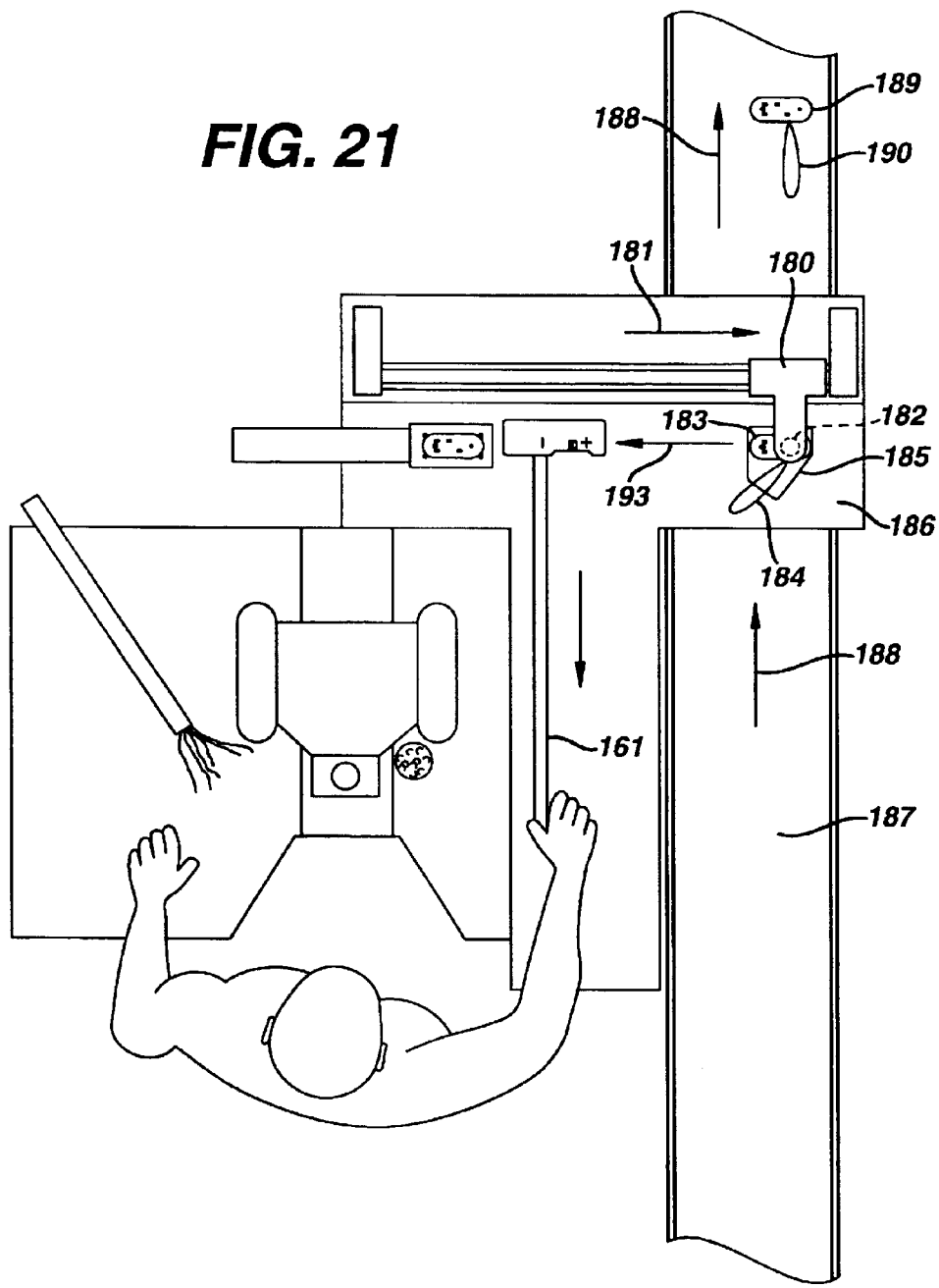

As seen in FIG. 21, the vacuum cup pick-up 182 is elevated and driven in the direction of arrow 181 to a fixed stop (not shown) that centers the package 183 with needles (not shown) and suture 184 over the opening 185 in the cover plate 186. The plate 186 extends, elevated, over the conveyor 187, said conveyor moving in the direction of arrows 188. The hole 185 in said cover plate allows vertical access to said conveyor therebelow.

The vacuum cup pick-up 182 is driven downward to a position just above, but not contacting, the conveyor 187. The vacuum source to vacuum cup pick-up 182 is disconnected, causing the package 183, with needles therein, and attached suture 184 to drop onto the conveyor 187. A similar package 189 and attached suture 190 from a previous machine cycle are shown for illustration.

The pick-up head 180 is driven in the direction of arrow 193 to a start position 165 illustrated in FIG. 19. The needle block is driven in the direction of arrow 192, along a linear slide 161, to a position 277 (FIG. 19) in preparation to repeat the machine cycle. The hopper shuttle 157 (FIG. 18) is driven in the direction of arrow 158, thereby feeding a new package molding 159, also in preparation to repeat the machine cycle.

Figure 22:
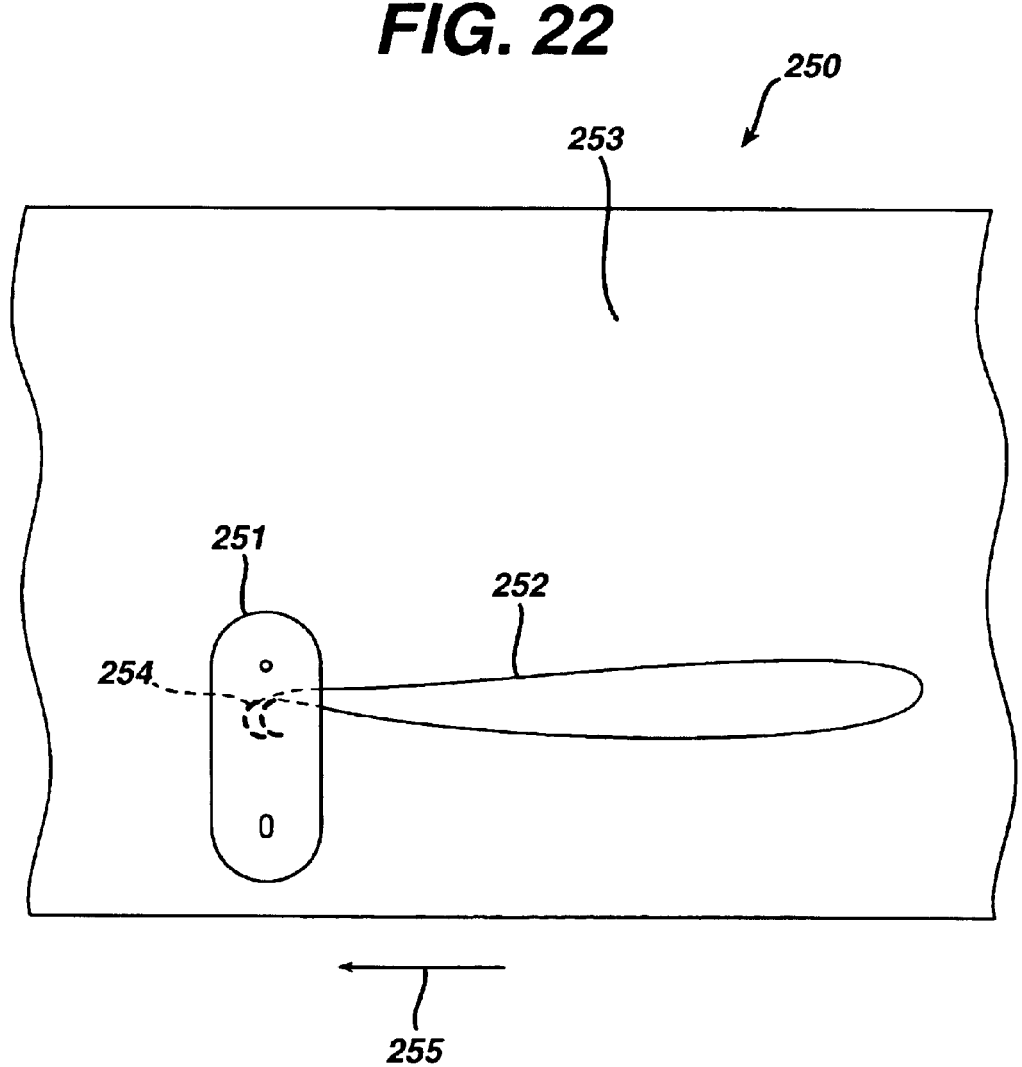
FIG. 22 is a view of an automatically assembled package in transit on the machine conveyor to the winding machine.

FIG. 22 illustrates an enlarged view of the package and needle/suture assembly 250 as it is discharged from the individual inserter workstation, placed on the moving conveyor 253, and in transit to the packaging machine. The package 251 is needle-side down, and the suture 252 trails therebehind, positioned to be picked up manually by the packaging machine operator.

FIG. 23 illustrates the working condition of the invention applied to surgical suture manufacturing, whereby four needle swaging workstations load swaged sutures into their respective needle blocks 202. The invention automatically assembles package moldings to the needles 203, and feeds same onto the continuously moving conveyor 205.

The conveyor 205, moving in the direction of arrow 204, transports the package assemblies 206 to within reach of the packaging machine loading operator 201.

Although this invention has been shown and described with respect to detailed embodiments thereof, it will be understood by those skilled in the art that various changes in form and detail thereof may be made without departing from the spirit and scope of the claimed invention.

We claim:

1. An apparatus for loading surgical needles into surgical suture packages, comprising:

a machine frame;

a needle block member having a top surface and a bottom surface, said needle block member slidably mounted to the frame;

a plurality of needle guide members extending up from the top surface of the needle block member, said guide members spaced apart to receive at least one surgical needle, said needle guide members having contact surfaces, said guide members additionally spaced apart to receive at least one needle park;

a shuttle member having a top, slidably mounted to the frame for engaging and moving a suture package; and, a pick-up head slidably mounted to the frame for picking up the package from the shuttle member, and contacting the package with the needle block member such that the needle park of the package is engaged between the needle guide members, wherein said pick-up head is moveable horizontally as well as vertically, and wherein said third rail is mounted to the frame.

2. The apparatus of claim 1 additionally comprising a conveyor belt, such that the pick-up head can be moved to release a package thereon.

3. The apparatus of claim 1 wherein the pick-up head comprises a vacuum chamber.

4. The apparatus of claim 1 wherein the needle block member additionally comprises a plurality of magnets mounted into the bottom surface.

5. The apparatus of claim 1 additionally comprising a groove extending into the top surface of the needle block between the needle guide members.

6. A method of loading surgical needles into surgical suture packages, the method comprising:

providing a suture package comprising a member having a top and a bottom, and a needle park extending from the top of the member;

providing a surgical needle assembly comprising a surgical needle and a suture mounted thereto;

providing an apparatus for loading surgical needles into surgical suture packages, comprising:

a machine frame;

a needle block member having a top surface and a bottom surface, said block member slidably mounted to the frame;

a plurality of needle guide members extending up from the top surface of the needle block member, said guide members spaced apart to receive at least one surgical needle, said needle guide members having contact surfaces, said guide members additionally spaced apart to receive at least one needle park;

a shuttle member having a top, slidably mounted to the frame for engaging and moving a suture package; and, a pick-up head slidably mounted to the frame for picking up the package from the shuttle member, and contacting the package with the needle block member such that the needle park of the package is engaged between the needle guide members, wherein said pick-up head is moveable horizontally as well as vertically;

placing the surgical needle into a space between the needle guide members on the needle block member and moving the needle block member to the loading position;

engaging the top of the package with the top of the shuttle member and moving the shuttle member and package to a transfer position;

moving the pick-up head to the transfer position and engaging the bottom of the package with the pick-up head;

moving the pick-up head and package to the loading position such that the package and needle perk is in alignment with the needle block member and needle guide members;

moving the pick-up head and package down such that the top of the package contacts the top surface of the needle block member, and the needle park is at least partially contained in a space between the needle guide members, thereby causing the needle to be engaged in the needle park of the package;

moving the pick-up heed and package containing needles in the needle park from the needle block member to a discharge position; and, releasing the package containing the needle in the needle park from the pick-up head at the discharge position.

7. The method of claim 6 wherein the apparatus additionally comprises conveyor belt, such that the pick-up head when moved to the discharge position releases a package thereon.

8. The method of claim 6 wherein the pick-up head comprises a vacuum chamber.

9. The method of claim 6 wherein the needle block member additionally comprises a plurality of magnets mounted into the bottom surface.

10. The method of claim 6 wherein the needle block additionally comprises a groove extending into the top surface between the needle guide members.

11. The method of claim 6 additionally comprising the step of transporting the package containing a needle in a needle park to a winder packaging machine.

* * * * *